United States Patent
Torres et al.

(10) Patent No.: US 10,438,341 B2
(45) Date of Patent: Oct. 8, 2019

(54) APPARATUS FOR DETECTING CORROSION IN AN ARTICLE

(71) Applicant: SIKORSKY AIRCRAFT CORPORATION, Stratford, CT (US)

(72) Inventors: Myra Torres, Pittsford, NY (US); Avinash Sarlashkar, Pittsford, NY (US); Michael J. Moore, Rochester, NY (US); Maksim Bobrov, Rochester, NY (US); Carl Palmer, Pittsford, NY (US); Michael J. Bluett, Canandaigua, NY (US); Jeremy W. Sheaffer, Ames, IA (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 0 days.

(21) Appl. No.: 15/509,606

(22) PCT Filed: Sep. 24, 2015

(86) PCT No.: PCT/US2015/051911
§ 371 (c)(1),
(2) Date: Mar. 8, 2017

(87) PCT Pub. No.: WO2016/053743
PCT Pub. Date: Apr. 7, 2016

(65) Prior Publication Data
US 2017/0294008 A1    Oct. 12, 2017

Related U.S. Application Data

(60) Provisional application No. 62/056,786, filed on Sep. 29, 2014.

(51) Int. Cl.
*G06T 7/00* (2017.01)
*G02B 27/00* (2006.01)
(Continued)

(52) U.S. Cl.
CPC .............. *G06T 7/001* (2013.01); *G01B 11/22* (2013.01); *G01N 17/006* (2013.01);
(Continued)

(58) Field of Classification Search
USPC ....................................................... 382/190
See application file for complete search history.

(56) References Cited

U.S. PATENT DOCUMENTS

| | | | | |
|---|---|---|---|---|
| 5,894,345 A | * | 4/1999 | Takamoto | G01N 21/8903 356/237.1 |
| 6,420,867 B1 | * | 7/2002 | Goldfine | G01N 27/9046 324/239 |

(Continued)

FOREIGN PATENT DOCUMENTS

| | | |
|---|---|---|
| EP | 1597566 B1 | 4/2008 |
| WO | 2007044725 A3 | 10/2005 |
| WO | 2012122467 A1 | 9/2012 |

OTHER PUBLICATIONS

Notification of Transmittal of the International Search Report for application PCT/US2015/051911 dated Nov. 7, 2015, Received Dec. 18, 2015; 8 pages.

(Continued)

*Primary Examiner* — Jerome Grant, II
(74) *Attorney, Agent, or Firm* — Cantor Colburn LLP

(57) ABSTRACT

A system and method of detecting, quantifying, and characterizing corrosion and degradation of an article, includes receiving signals indicative of a stack of images of a surface of the article; determining depth and nature of features in the stack of images; generating a surface model of the article in response to the determination of the depth and the nature of features; determining features of interest from the surface model; comparing the features of interest with predetermined information on the article; and characterizing the (Continued)

article as corroded or degraded in response to the comparisons of the features of interest.

19 Claims, 5 Drawing Sheets

(51) Int. Cl.
| | |
|---|---|
| G01B 11/22 | (2006.01) |
| G01N 17/00 | (2006.01) |
| G01N 17/04 | (2006.01) |
| G06F 3/0481 | (2013.01) |
| G02B 3/00 | (2006.01) |

(52) U.S. Cl.
CPC ....... G01N 17/043 (2013.01); G02B 27/0075 (2013.01); G06F 3/0481 (2013.01); *G02B 3/0006* (2013.01); *G06T 2200/24* (2013.01); *G06T 2207/10028* (2013.01); *G06T 2207/10052* (2013.01); *G06T 2207/30136* (2013.01)

(56) References Cited

U.S. PATENT DOCUMENTS

| | | | |
|---|---|---|---|
| 6,792,357 | B2 | 9/2004 | Menon et al. |
| 7,312,859 | B2 | 12/2007 | Koudelka et al. |
| 7,872,796 | B2 | 1/2011 | Georgiev |
| 8,033,164 | B2 | 10/2011 | Dermody et al. |
| 8,176,786 | B2 | 5/2012 | Sohn et al. |
| 8,237,548 | B2 | 8/2012 | Fay et al. |
| D666,660 | S | 9/2012 | Amit et al. |
| 8,306,760 | B1 | 11/2012 | Koudelka et al. |
| 8,332,165 | B1 | 12/2012 | Tat |
| 2003/0202089 | A1 | 10/2003 | Alhadef et al. |
| 2006/0019409 | A1 | 1/2006 | Nelson et al. |
| 2006/0288756 | A1 | 12/2006 | De Meurechy |
| 2008/0007467 | A1 | 1/2008 | Seo |
| 2008/0074676 | A1 | 3/2008 | Koudelka et al. |
| 2008/0289423 | A1* | 11/2008 | Gordon ................ G01N 29/069 73/602 |
| 2011/0054813 | A1* | 3/2011 | Moreau ............. G01N 27/9006 702/59 |
| 2012/0279599 | A1 | 11/2012 | Gluskin et al. |
| 2012/0300097 | A1 | 11/2012 | Ng et al. |
| 2012/0320159 | A1* | 12/2012 | Torres .................. G06T 7/0006 348/46 |
| 2014/0267627 | A1 | 9/2014 | Freeman et al. |
| 2016/0155712 | A1* | 6/2016 | Gietler .................... H01L 23/58 257/48 |
| 2016/0245738 | A1* | 8/2016 | Leyte Guerrero ........ C25F 3/14 |
| 2017/0315067 | A1* | 11/2017 | Mandrake ............ G01N 23/203 |
| 2017/0323835 | A1* | 11/2017 | Ogawa .................... H01L 22/34 |
| 2017/0336328 | A1* | 11/2017 | Gupta ................ G01N 21/8422 |

OTHER PUBLICATIONS

Written Opinion of the International Searching Authority for application PCT/US2015/051911 dated Nov. 7, 2015, Received Dec. 18, 2015; 4 pages.

Extended European Search Report; European Application No. 15846861.1; dated Mar. 14, 2018; 10 Pages.

* cited by examiner

APPARATUS FOR DETECTING CORROSION IN AN ARTICLE

CROSS REFERENCE TO RELATED APPLICATIONS

This application is a National Stage application of PCT/US2015/051911, filed Sep. 24, 2015, which claims the benefit of U.S. Provisional Application No. 62/056,786, filed Sep. 29, 2014, both of which are incorporated by reference in their entirety herein.

BACKGROUND

The subject matter disclosed herein relates generally to the field of non-destructive inspection and, more particularly, to a handheld apparatus for inspection of a metallic article in the field for detecting, quantifying, and characterizing corrosion and degradation.

DESCRIPTION OF RELATED ART

Pitting corrosion is a surface degradation mechanism in metallic materials. This type of corrosion is insidious in aviation and vehicle structures, as it can significantly reduce the reliability of safety-critical components, such as the dynamic components for drive-train on rotorcraft as well as (non-dynamic) load-bearing structural members. The understanding of the severity of corrosion pits, i.e., the corrosion-pit diameter and depth quantity as well as the nearness of one corrosion pit to the next, is extremely important for structural maintenance of an aviation fleet, spares management, aircraft availability, and safety.

Rotorcraft are routinely inspected to detect the presence of corrosion of critical components. Current non-destructive methods for corrosion detection on rotorcraft do not lend themselves to automated, in-field use, which can produce subjective results and lead to poor maintenance decisions. These approaches either depend on the subjective evaluation of pitting corrosion observed by the maintenance crew or rely on intense post processing using other detection methods (surface impressions, surface images, ultrasound, acoustic emission, eddy current-electromagnetic testing, infra-red thermography, laser optics, etc.). These approaches are not field friendly, and often require complex setup and training. Field technicians often have to supplement their inspection with online microscopic analysis of the surfaces. Standard field micro-analysis devices provide a two-dimensional image of the three-dimensional surface under magnification, but such images do not provide pit depth information, which is often key to effective corrosion detection. Also, current testing approaches do not possess the resolution necessary to effectively detect and characterize surface pitting and identify trend progressions; all information needed for an effective rotorcraft—or other vehicle—maintenance program.

Once corrosion is detected, a repair or replacement decision needs to be made. Currently, this decision is qualitative and can result in high cost of ownership due to potentially unnecessary hardware replacements. Further, such maintenance action reduces the availability of the rotorcraft while repairs are made. A hand-held apparatus for in-field inspection and detection of corrosion that has a quantitative and robust methodology would be well received in the art.

BRIEF SUMMARY

According to one aspect of the invention, a system to detect, quantify, and characterize corrosion and degradation having a graphical user interface (GUI); an article; an inspection device configured to receive a stack of images from a surface of the article; memory having one or more instructions; and a processor that is configured to execute the one or more instruction and cause the system to: determine a depth and nature of features in the stack of images; generate a surface model of the article in response to the determining of the depth and the nature of features; determine features of interest from the surface model; compare the features of interest with predetermined information; and characterize the article as corroded or degraded in response to the comparison of the features of interest.

According to another aspect of the invention, a computer-implemented method of detecting, quantifying, and characterizing corrosion and degradation of an article, includes an inspection device with a graphical user interface having a computing device: receiving, with a processor, signals indicative of a stack of images of a surface of the article; determining, with the processor, depth and nature of features in the stack of images; generating, with the processor, a surface model of the article in response to the determination of the depth and the nature of features; determining, with the processor, features of interest from the surface model; comparing, with the processor, the features of interest with predetermined information on the article; and characterizing, with the processor, the article as corroded or degraded in response to the comparisons of the features of interest.

According to another aspect of the invention, a graphical user interface having a processor and memory with instructions that when executed by the processor cause the graphical user interface to: receive signals indicative of a stack of images of a surface of an article; determine depth and nature of features in the stack of images; generate a surface model of the article in response to the determination of the depth and the nature of features; determine features of interest from the surface model; compare the features of interest with predetermined information on the article; and characterize the article as corroded or degraded in response to the comparisons of the features of interest.

In addition to one or more of the features described above, or as an alternative, further embodiments could include a processor that is configured to compare the features of interest with defined features from corroded and degraded samples in coupon test data.

In addition to one or more of the features described above, or as an alternative, further embodiments could include a processor that is configured to compare the features of interest with a defined parameter from standards.

In addition to one or more of the features described above, or as an alternative, further embodiments could include a processor that is configured to receive the stack of images as multiple images from a micro lens array.

In addition to one or more of the features described above, or as an alternative, further embodiments could include a processor that is configured to perform a spatial frequency domain analysis on the stack of images.

In addition to one or more of the features described above, or as an alternative, further embodiments could include a processor that is configured to determine relative depth information in the stack of images.

In addition to one or more of the features described above, or as an alternative, further embodiments could include a processor that is configured to multiply the relative depth information with a measured focal length to provide absolute values of depth.

In addition to one or more of the features described above, or as an alternative, further embodiments could include an inspection device that has interchangeable objective lenses with one or more of a differing magnification, differing focal lengths, differing apertures, differing field of view, and adjustable optical parameters.

In addition to one or more of the features described above, or as an alternative, further embodiments could include an inspection device that has a lens that changes the image viewing angle for use in in-accessible areas.

In addition to one or more of the features described above, or as an alternative, further embodiments could include an inspection device that has an internal self-contained variable light source that is configured to illuminate the article.

In addition to one or more of the features described above, or as an alternative, further embodiments could include a processor that is configured to define a virtual feducial for measurement repeatability.

Technical effects of the embodiments described above are quantitative and robust methodology for detecting, quantifying, and characterizing corrosion and degradation of safety critical articles in field applications. Additionally, embodiments described above can eliminate the subjective nature of current inspection processes and can bring consistency to the inspection process, thereby increasing the accuracy of corrosion and degradation inspections and potentially reducing the number of unnecessary component replacements and associated costs.

Other aspects, features, and techniques of the invention will become more apparent from the following description taken in conjunction with the drawings.

BRIEF DESCRIPTION OF THE SEVERAL VIEWS OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which like elements are numbered alike in the several FIGURES:

DETAILED DESCRIPTION

Figure 1:
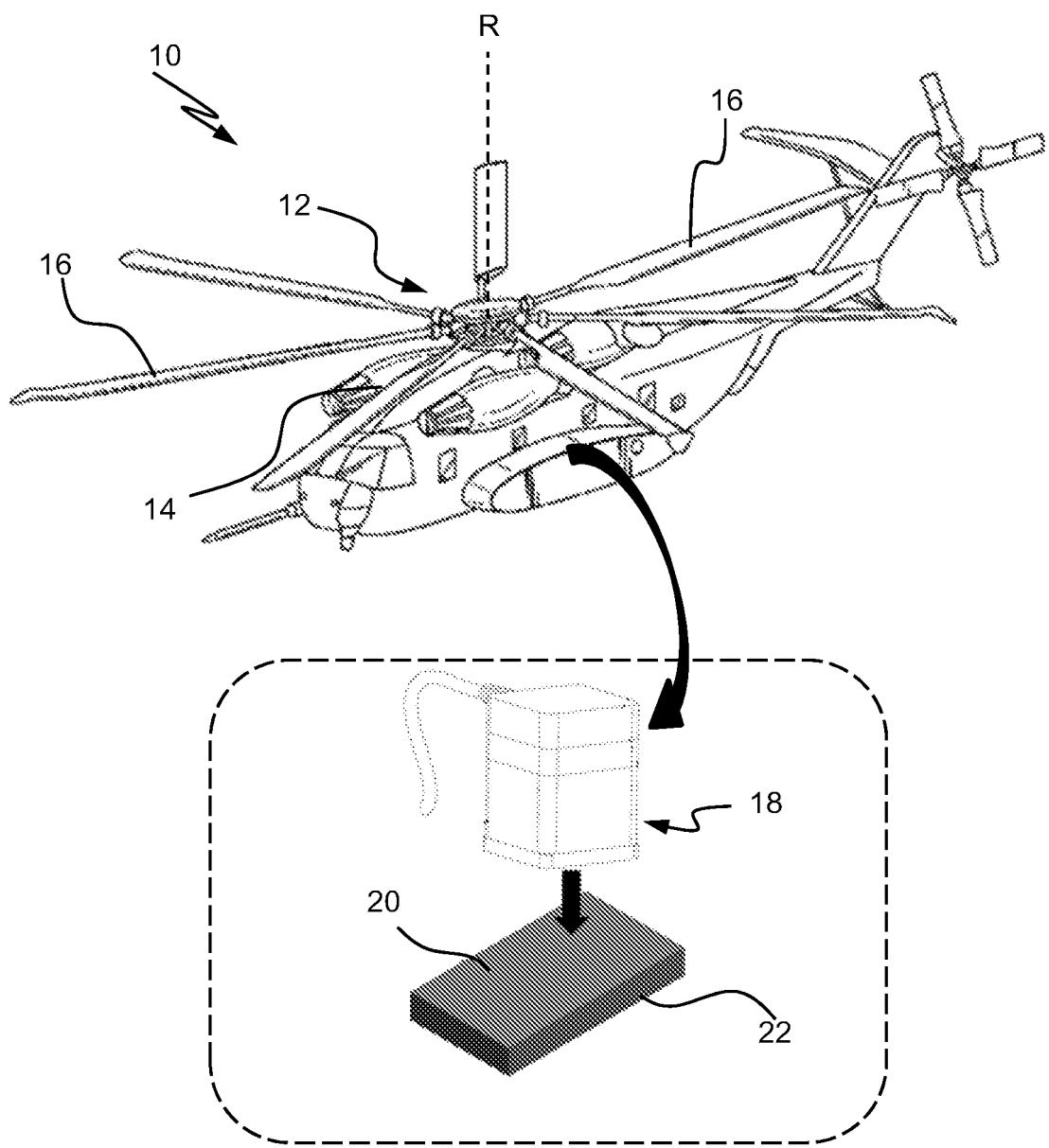
FIG. 1 is a perspective view of an exemplary aircraft for use with embodiments of the invention.

Referring to the drawings, FIG. 1 illustrates a rotary-wing aircraft 10 or helicopter with a hand-held corrosion inspection system 18 (hereinafter "inspection system 18") that is used for non-destructive inspection of a surface of a metal component of aircraft 10 for detecting, quantifying, and characterizing corrosion and degradation in accordance with an embodiment of the invention. As shown, rotary-wing aircraft 10 includes a main rotor assembly 12 that is driven about an axis of rotation R by one or more engines 14. The main rotor assembly includes a multiple of rotor blades 16 mounted to rotor assembly 12 and are driven for rotation about axis R through a main gearbox (not shown for clarity).

Also illustrated, inspection system 18 is provided as a hand-held apparatus that can be used for inspection of a surface 20 of aircraft 10 by an operator or technician in the field. In an embodiment, inspection system 18 includes a field array camera with hardware and software for detecting and quantifying, in an embodiment, pitting corrosion damage or other degradation on surface 20 of a metal article 22 of aircraft 10, as will be described further in embodiments herein. In exemplary embodiments, inspection system 18 can include one or more light field array cameras in a low-profile hand-held apparatus having magnification optics and algorithms to identify pitting corrosion and other degradation, for example, uniform corrosion, crevice corrosion, galvanic attack, erosion, fretting, exfoliation, de-alloying, stress corrosion cracking, and corrosion fatigue, to determine a diameter and depth of pitting, stress fractures, or other wear, and to identify a number of pits on surface 20. The inspection system 18 may be a hand held, portable unit, having the components of FIG. 2. While inspection system 18 is shown and described being used with a rotary-wing aircraft 10, inspection system 18 may also be used to detect corrosion or degradation on static and dynamic component surfaces of metal and non-metal articles and structures. For example, inspection system 18 can be used to determine degradation of corrosion protection coatings such as, for example, paint or primer coatings, to determine types of corrosion including uniform corrosion, crevice corrosion, galvanic attack, erosion, fretting, exfoliation, de-alloying, stress corrosion cracking, and corrosion fatigue, to determine particles in oil including estimating the number, shape, size of particles, and to determine particles in water including estimating the number (turbidity), shape, size of particles.

Figure 2:
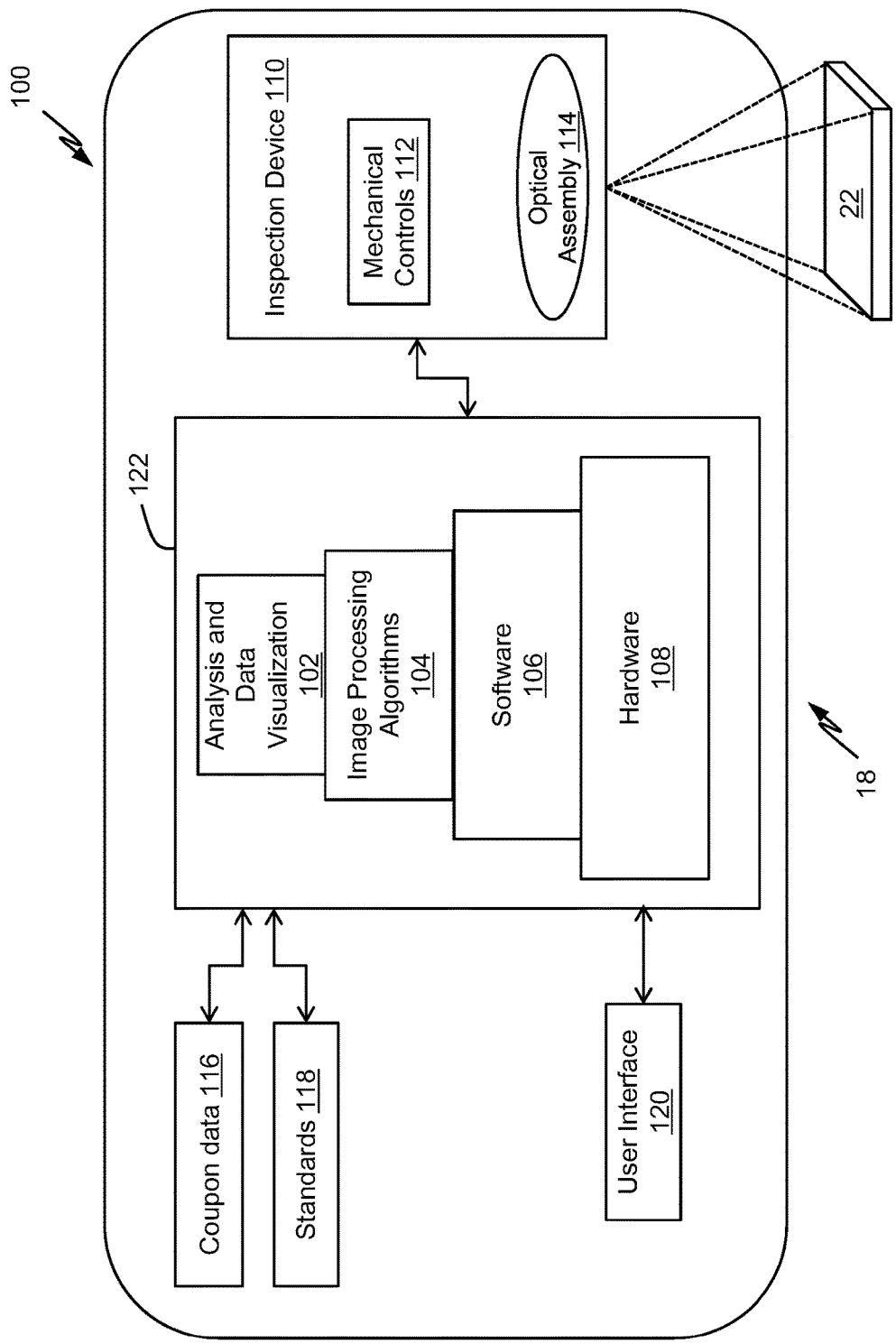
FIG. 2 is block diagram of an exemplary architecture of a monitoring system for use with embodiments of the invention.

FIG. 2 is block diagram of an exemplary architecture 100 used in inspection system 18 for the non-destructive detection, quantification, and characterization of corrosion and degradation on article 22 such as those found in aircraft 10 (FIG. 1). Architecture 100 includes hardware 108, which may be implemented using known processing devices, such as a microprocessor (e.g., a digital signal processor (DSP)) or a field programmable grid array (FPGA)). Hardware 108 interfaces with an inspection device 110. Inspection device 110 is a light field array camera and includes optical assembly 114, a light source, a detector (e.g., a charge-coupled device (CCD)) and other components as described in further detail herein. Hardware 108, software 106, algorithms 104, and data visualization 102 are collectively represented by processing unit 122.

Hardware 108 can include a main memory such as random access memory (RAM), and may also include a secondary memory. The secondary memory may include, for example, one or more databases, a hard disk storage unit and one or more removable storage units representing a floppy disk drive, a magnetic tape drive, an optical disk drive, a removable memory chip (such as an erasable programmable read only memory (EPROM), or programmable read only memory (PROM)) and associated socket, and the like which allow software and data to be transferred from a removable storage unit to inspection system 18. The removable storage unit reads from and writes to a hard disk storage unit in a well-known manner. As will be appreciated, the removable storage unit includes a computer usable storage medium having stored therein software and data.

Software 106 has algorithms for analyzing images from optical assembly 114 and rendering a graphical user interface (GUI) 120 for displaying the analysis results. For a Digital Signal Processing (DSP) solution, the software 106 would include a minimalistic operating system for supporting the multimedia libraries and drivers for the display and optics interfaces.

Inspection device 110 houses a detector, lenses, and a light source for illuminating the article to be inspected. A single camera with interchangeable objective lenses can be used. Photoreceptors such as, e.g., a complementary metal-oxide semiconductor (CMOS), charge-coupled device (CCD), or film can be used to store sub-images captured through the micro lens array of optical assembly 114. Image processing algorithms 104 are used to process the acquired sub-images from optical assembly 114.

The image processing algorithms 104 can select a series of sub-images across several fields of depth for two-dimensional (2D) analysis and generate a depth map for three-dimensional (3D) analysis, as described in further detail herein. Image filtering, alignment, enhancement, etc., may be performed by image processing algorithms 104 on the sub-image data. Image processing can include applying a Fast Fourier Transform (FFT) on the sub-image data.

Analysis and data visualization module 102 uses the information from image processing algorithms 104 to detect, quantify, and characterize corrosion and degradation such as, for example, to determine pitting corrosion, to determine a diameter and depth of pitting, and to identify a number of pits on surface of article 22. The analysis and data visualization module 102 measures features from the 2D image and a 3D depth map, and compares these features to standards 118 or coupon data 116. Standards 118 and coupon data 116 may be loaded into inspection system 18 remotely (e.g., via software update) so that the inspection system 18 is configurable for inspection of a myriad of articles. In the example, standards 118 may represent acceptable standards of materials for Department of Defense (DOD) aircraft, e.g., surface roughness of metal surfaces in military applications. Also, coupon data 116 may include coupon test data that includes identified corrosion having defined features in corroded samples, which are substantially similar to a surface of article 22.

Figure 3:
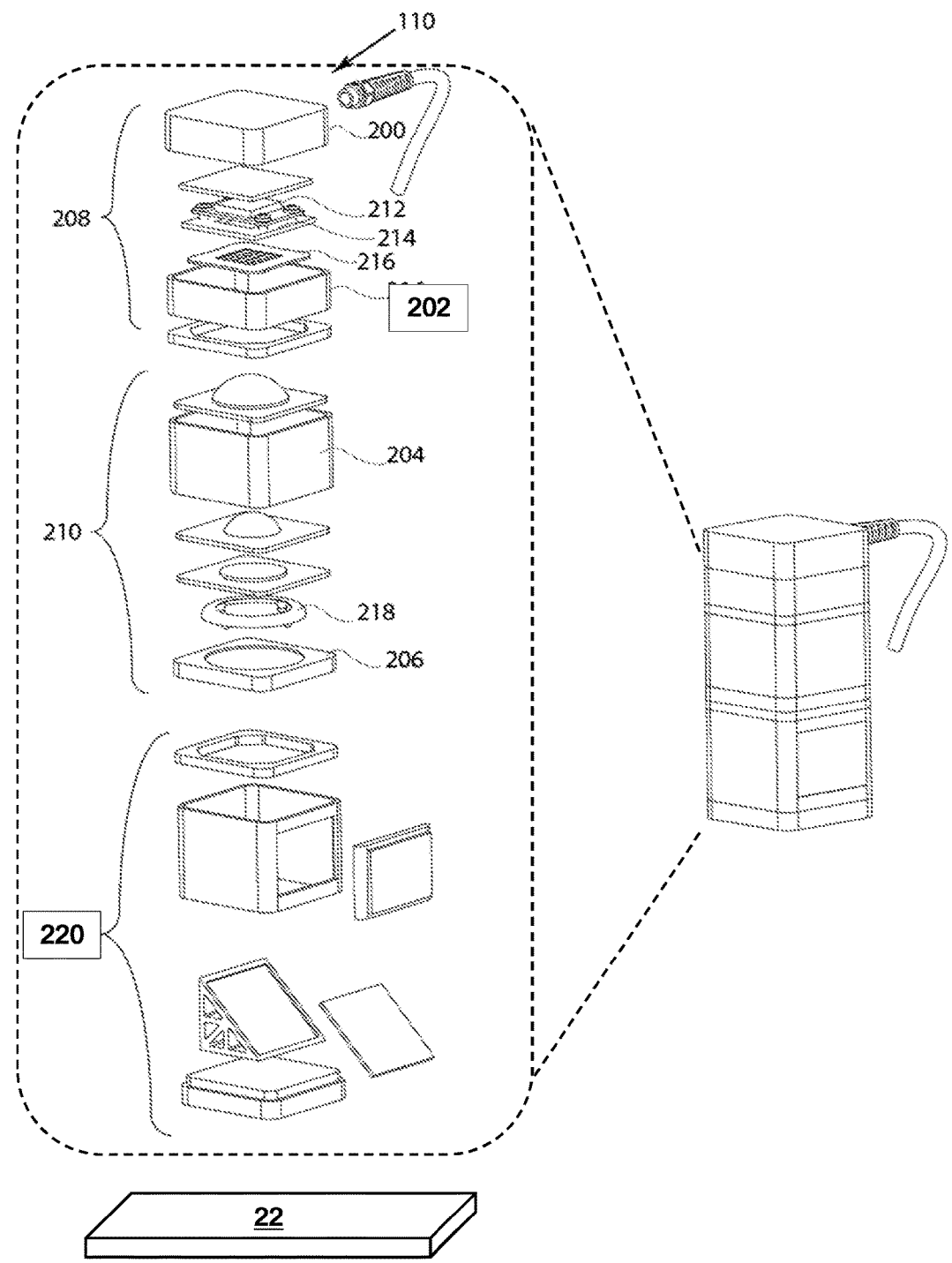
FIG. 3 is an exploded view of an inspection device in accordance with an embodiment of the invention.

FIG. 3 is an exploded view of an exemplary inspection device 110 in inspection system 18 (FIG. 2) in accordance with an embodiment of the invention. Inspection device 110 is a portable hand-held device that includes a housing body made from housing portions 200, 202, 204, and 206. Housing portions 202-206 are coupled together to enclose stationary camera 208 and objective lens or lenses 210 (collectively referred to as "objective 210"). Objective 210 can include a single lens or multiple lenses working together, for example, through a lens system to provide differing or varying magnification. Objective 210 may have a fixed or adjustable focal length, aperture, field of view, and magnification. Inspection device 110 may contain a mirror or prism 220 that allows camera 208 to image surfaces that are inaccessible at a straight-in angle. In an embodiment, a technician may use interchangeable objective lenses of varying focal lengths for objective 210. Light source 218 within objective 210 illuminates article 22 to be inspected. Stationary camera 208 has a micro lens array 216, which is a 2D matrix of square, microscopic lenses. Micro lens array 216 is mounted between objective 210 and a photoreceptor array 212, behind aperture 214, with a separation distance of no more than the focal length of one of the micro lenses between the two arrays. Photoreceptor array 212 can be a CCD, a CMOS device, or film. Objective 210 focuses incident light from article 22 onto micro lens array 216. Micro lens array 216 performs optical sectioning to produce images at various focal lengths of the surface of article 22.

The sub-images corresponding with each micro lens contain information to reconstruct versions of an image of article 22 with various virtual focal depths and depths of field. The sum of this information is called a light field. Information on the relative depths of field from the sub-images is processed through image process algorithm 104 (FIG. 2) to generate a depth map that is orthogonal to surface of article 22. Further, the depth map is calibrated against coupon data 116 (FIG. 2) and standards 118 (FIG. 2) to quantify absence or presence of corrosion on article 22.

Figure 4:
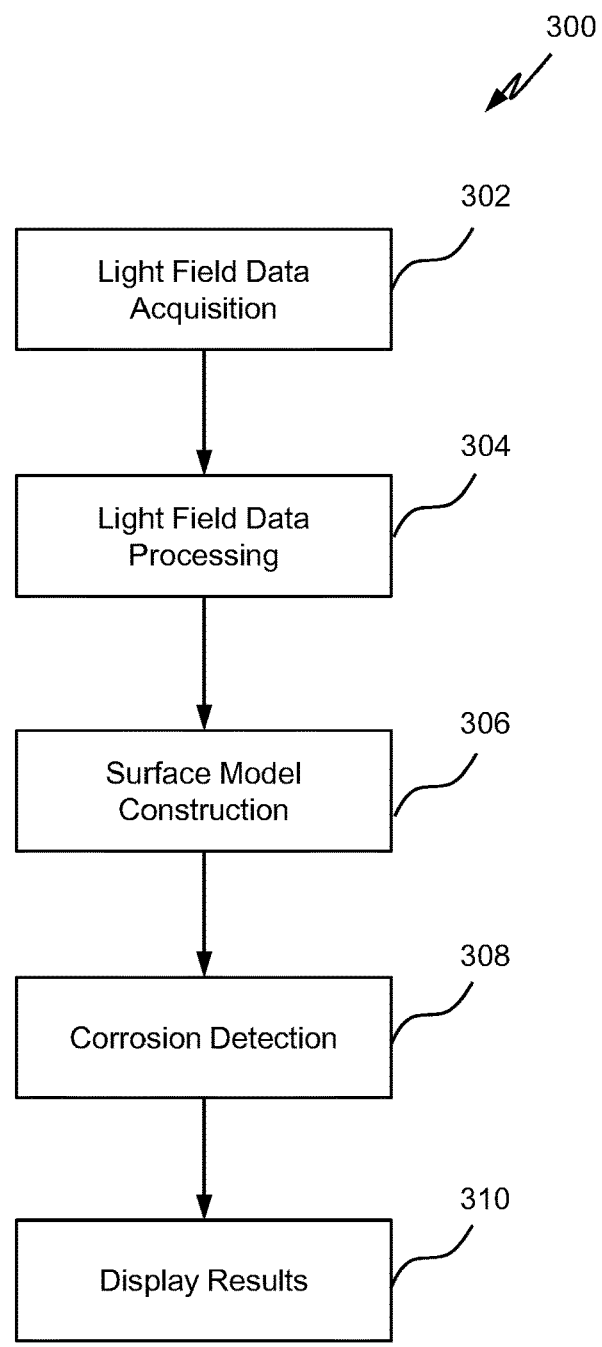
FIG. 4 is an exemplary flow diagram for inspecting, detecting, and quantifying corrosion in accordance with an embodiment of the invention.

FIG. 4 is an exemplary process 300 for detecting and quantifying corrosion in an article that is performed by inspection system 18 (FIG. 1) in accordance with an embodiment of the invention. As such, FIG. 2 is also being referenced in the description of the exemplary process 300 of FIG. 4.

As shown, the exemplary process 300 is initiated in block 302 where light field data is acquired by inspection device 110 for an article 22 being inspected. For example, a technician presses a button on inspection device 110 to launch device 110 after placing inspection device 110 on the surface of article 22. Inspection system 18 activates light source 218 (FIG. 3) to illuminate article 22 (FIG. 3). Objective 210 focuses incident light, from article 22, through a micro lens array 216, onto a photoreceptor 212 (FIG. 3). Images are received from each micro lens by photoreceptor 212 and stored as 2D images in memory onboard inspection system 18. These 2D images from each micro lens in micro lens array (2D sub-images) represent light field image data at different angle of incidences.

In block 304, the 2D light field data is analyzed to calculate depth and nature of features. Information from each sub-image is processed in order to determine a depth profile of features in the image data. A depth map is generated from the stack of images using transforms.

In block 306, a 3D surface model of article 22 is built from the processed data. For example, an inverse spatial frequency transform (e.g., Inverse Fourier Transform) is performed on the combined coefficients to form a fused image in an image space. Initially, images produces by each micro lens encodes parallax with respect to all other micro lenses. Extracted depth information from the images in the image space provide relative depth information, i.e., an object is in front of another object, and twice as far in front of another object, etc. A 3D model is then created by multiplying the relative depths by a known focal length used in calibration of objective 210 (FIG. 3) to provide an absolute value of depth. The 3D model provides a depth profile of objects of interest relative to the surface of the article 22 being inspected. Depth of features, and nature of features, for example, color and quantity are passed to data visualization 102 for classification in 308. In an embodiment, a 3D model of article 22 may be displayed to the technician on user interface 120.

In block 308, feature detection is performed on the 3D model in order to detect corrosion. The 3D model is analyzed to detect pitting corrosion by comparing a depth profile of a feature of interest in article 22 to corroded or degraded samples in coupon test data 116. In addition to the using coupon test data 116, or as an alternative, another embodiment could include comparing a depth profile of the feature of interest with defined parameters from standards 118. Features of interest are located, counted, and measured by comparison to coupon test data 116 or standards 118. In an embodiment, a virtual feducial for measurement repeatability can be defined from the features. A pattern is created by using vectors of minimum distance to a center point between all key features identified in a plane of view. This pattern of vectors represents a unique pattern that is stored in memory for future pattern recognition to locate inspection device 110. Thus a measurement or test can be repeated when this vector pattern is identified. This process of using a virtual feducial can be utilized for manual as well as automated movement of inspection device 110. If a feature of interest fails to meet the requirements of coupon test data 116 or standards 118, then the object of interest is pitting corrosion or other degradation and information on its location and size is stored in processing unit 122. Additionally, processing unit 122 can store a count of pits detected and determine "PASS" or "FAIL" of the article based on a comparison to coupon test data 116 or standards 118. In block 310, the results are classified and results are displayed to a technician. For example, features of interest that fail coupon test data 116 or standards 118 are identified on an image of the surface of article 22 by their location and size and "PASS" or "FAIL" labels are displayed to a technician on user interface 120. In an embodiment, a 3D model may also be displayed on user interface 120 in addition to or in lieu of the image of the surface of article 22. In an embodiment, pass and fail semantics may be communicated through text, indicator light, sound, etc.

Figure 5:
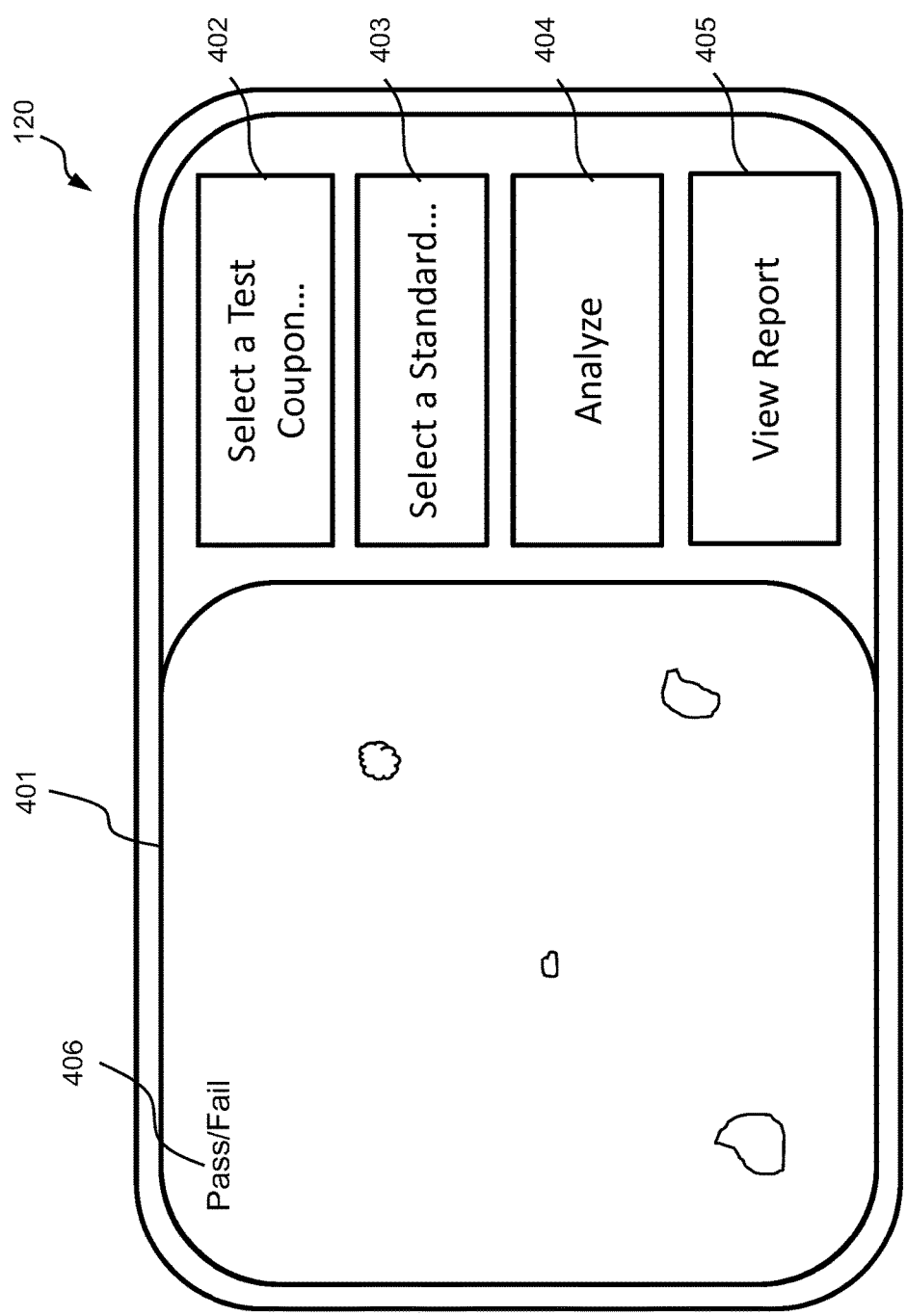
FIG. 5 illustrates an exemplary graphical user interface (GUI) in accordance with an embodiment of the invention.

The inspection results are displayed to the user in a simple and intuitive manner through a GUI. FIG. 5 is an exemplary GUI 120. GUI 120 may include an LCD screen attached to inspection device 110 (FIG. 3). This LCD screen may display images 401 captured from inspection device 110. On this screen, the user may also have the option to select a test coupon using input 402 or a standard to compare against using input 403. The user may also have the option to initiate process 300 (FIG. 4) for detecting and quantifying corrosion in an article using input 404 culminating in the display of inspection results 406. The user may also have the option to view an in-depth report using input 405. Inputs 402, 403, 404, and 405 may be text, mouse, touch, or any combination of these. This LCD screen may also serve as a means to control inspection device 110 (FIG. 3). The GUI 120 may be used to enter information about the article to be inspected, if specific parameters are needed to maximize the success rate of the inspection process, as well as control inspection device 110 (FIG. 3) as needed.

Embodiments of the hand-held inspection system provide many benefits to the technician or operator. Inspection standards and coupon test data are controlled through software; the technician does not have to be burdened by the nuances of acceptance criteria and can focus on the field application of detecting, quantifying, and characterizing corrosion and degradation on articles. The inspection system can eliminate the subjective nature of current inspection processes and can bring consistency to the inspection process thereby potentially reducing the number of unnecessary component replacements and associated costs.

The terminology used herein is for the purpose of describing particular embodiments only and is not intended to be limiting of the invention. While the description of the present invention has been presented for purposes of illustration and description, it is not intended to be exhaustive or limited to the invention in the form disclosed. For instance, aspects of the invention are not limited to rotorcraft, and can be used in any structures and articles. Many modifications, variations, alterations, substitutions or equivalent arrangements not hereto described will be apparent to those of ordinary skill in the art without departing from the scope and spirit of the invention. Additionally, while the various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A computer-implemented method of detecting, quantifying, and characterizing corrosion and degradation of an article, comprising:
   receiving, with a processor, signals indicative of a stack of images of a surface of the article;
   determining, with the processor, depth and nature of features in the stack of images;
   generating, with the processor, a surface model of the article in response to the determination of the depth and the nature of features;
   determining, with the processor, features of interest from the surface model;
   comparing, with the processor, the features of interest with predetermined information on the article;
   comparing the features of interest with defined features from corroded or degraded samples in coupon test data;
   characterizing, with the processor, the article as corroded or degraded in response to the comparisons of the features of interest; and
   displaying a characterization of the article resulting from said characterizing on a graphical user interface.

2. The computer-implemented method of claim 1, further comprising comparing the features of interest with defined parameters from standards.

3. The computer-implemented method of claim 1, further comprising receiving the stack of images as multiple images from a micro lens array.

4. The computer-implemented method of claim 1, wherein the determination of the depth of features further comprises performing a spatial frequency domain analysis on the stack of images.

5. The computer-implemented method of claim 1, wherein the determination of the depth of features further comprises determining relative depth information in the stack of images.

6. The computer-implemented method of claim 1, further comprising receiving the signals from the inspection device for a field inspection of the article.

7. The computer-implemented method of claim 1, further comprising receiving the signals from the inspection device with interchangeable objective lenses with one or more of differing magnification, differing focal lengths, differing apertures, differing field of view, and adjustable optical parameters.

8. The method of claim 1, the method further comprising:
   determining degradation in a protection coating selected from a group including painted coatings and primer coatings;
   determining a type of corrosion selected from a group including uniform corrosion, crevice corrosion, galvanic attack, erosion, fretting, exfoliation, dealloying, stress corrosion cracking, and corrosion fatigue;
   determining particles in oil including estimating one or more of number, shape, and size of the particles; and
   determining particles in water including estimating one or more of number, shape, and size of the particles.

9. The method of claim 1, further comprising providing a characterization of corrosion and degradation of the article on a graphical user interface.

10. The method of claim 1, further comprising acquiring light field data for the surface of the article including intensity information and directional information in light reflected from the surface of the article.

11. A computer-implemented method of detecting, quantifying, and characterizing corrosion and degradation of an article, comprising:
receiving, with a processor, signals indicative of a stack of images of a surface of the article;
determining, with the processor, depth and nature of features in the stack of images;
generating, with the processor, a surface model of the article in response to the determination of the depth and the nature of features;
determining, with the processor, features of interest from the surface model;
comparing, with the processor, the features of interest with predetermined information on the article;
characterizing, with the processor, the article as corroded or degraded in response to the comparisons of the features of interest; and
displaying a characterization of the article resulting from said characterizing on a graphical user interface,
wherein the determination of the depth of features further comprises determining relative depth information in the stack of images; and
further comprising multiplying the relative depth information with a measured focal length.

12. A system to detect, quantify, and characterize corrosion and degradation comprising:
a graphical user interface (GUI);
an article;
an inspection device configured to receive a stack of images from a surface of the article;
memory having one or more instructions; and
a processor that is configured to execute the one or more instruction and cause the system to:
determine a depth and nature of features in the stack of images;
generate a surface model of the article in response to the determining of the depth and the nature of features;
determine features of interest from the surface model;
compare the features of interest with predetermined information;
compare the features of interest with defined features from corroded and degraded samples in coupon test data; and
characterize the article as corroded or degraded in response to the comparison of the features of interest.

13. The system of claim 12, wherein the processor is configured to compare the features of interest with a defined parameter from standards.

14. The system of claim 12, wherein the processor is configured to receive the stack of images as multiple images from a micro lens array.

15. The system of claim 12, wherein the processor is configured to determine relative depth information in the stack of images.

16. The system of claim 12, wherein the inspection device includes interchangeable objective lenses with one or more of a differing magnification, differing focal lengths, differing apertures, differing field of view, and adjustable optical parameters.

17. The system of claim 12, wherein the processor is configured to:
determine degradation in a protection coating selected from a group including painted coatings and primer coatings;
determine a type of corrosion selected from a group including uniform corrosion, crevice corrosion, galvanic attack, erosion, fretting, exfoliation, dealloying, stress corrosion cracking, and corrosion fatigue;
determine particles in oil including estimating one or more of number, shape, and size of the particles; and
determine particles in water including estimating one or more of number, shape, and size of the particles.

18. The system of claim 12, wherein the processor is configured to provide a characterization of corrosion and degradation of the article on the GUI.

19. The system of claim 12, wherein the inspection device is a light field camera array to provide the stack of images to the inspection system.

* * * * *